United States Patent [19]

Evans

[11] Patent Number: 5,698,188

[45] Date of Patent: Dec. 16, 1997

[54] GEL AIR FRAGRANCING COMPOSITION AND METHOD FOR MAKING THE SAME

[75] Inventor: Carol A. L. Evans, Hull, United Kingdom

[73] Assignee: Reckitt & Colman Products Limited, London, England

[21] Appl. No.: 596,777

[22] Filed: Feb. 5, 1996

[30] Foreign Application Priority Data

Feb. 7, 1995 [GB] United Kingdom .................. 9502318

[51] Int. Cl.$^6$ .............................. A61K 7/46; A61K 9/01; B01J 13/00

[52] U.S. Cl. .................. 424/76.4; 252/315.3; 512/2; 512/4

[58] Field of Search ............... 252/315.3; 424/76.4; 512/2, 4

[56] References Cited

U.S. PATENT DOCUMENTS

| | | | |
|---|---|---|---|
| 2,927,055 | 3/1960 | Lanzet | 424/76.4 |
| 3,767,787 | 10/1973 | Segal | 252/315.3 X |
| 4,178,264 | 12/1979 | Streit et al. | 252/315.3 |
| 4,755,377 | 7/1988 | Steer | 424/76.4 |

*Primary Examiner*—Richard D. Lovering
*Attorney, Agent, or Firm*—Fish & Richardson P.C.

[57] ABSTRACT

An aqueous self-supporting gel composition is provided, which consists essentially of:

a) 1 to 20% of a fragrance material (preferably a fragrant oil), b) 2 to 10% of a carrageenan constituent, c) 0 to 2% of a preservative, d) 0 to 2% of a coloring agent, and e) 0 to 0.5% surfactant, the balance being water and all percentages being by weight of the composition.

10 Claims, No Drawings

GEL AIR FRAGRANCING COMPOSITION AND METHOD FOR MAKING THE SAME

The present invention relates to a fragrance composition and, in particular, to a gel-type fragrance composition and a method for preparing the composition.

Fragrance compositions are commonly used as air fresheners, and can be provided in gel form. Such compositions would normally contain gelling agents and perfume, together with a solvent, surfactant, and other ingredients.

According to the invention, there is provided an aqueous self-supporting gel composition consisting essentially of:

a) 1 to 20% of a fragrance material (preferably a fragrant oil),
b) 2 to 10% of a carrageenan constituent,
c) 0 to 2% of a preservative,
d) 0 to 2% of a coloring agent, and
e) 0 to 0.5% surfactant, the balance being water and all percentages being by weight of the composition.

By "self-supporting gel" is meant a gel which, at ambient temperature, is of sufficient rigidity that it is firm, is not capable of flowing and maintains its structure. Such a gel can be used as a stick without support means, and is able to stand alone.

Carrageenan is a product derived previously from seaweed and is a linear polysaccharide. The term is well known in the art. Carrageenan may also be synthetically produced.

Suitably, a mixture of kappa, iota and lambda polysaccharide carrageenans may be present in the gel composition in accordance with the invention.

By "carrageenan constituent" is meant a carrageenan gelling agent composition comprising one or more carrageenan compounds, optionally with lesser amounts of one or more other constituents. The carrageenan constituent may comprise a composition which is essentially 100% by weight of one or more carrageenan compounds. Also, the carrageenan constituent may be a composition which includes at least about 50% by weight, more desirably at least about 70% by weight of one or more carrageenan compounds, in addition to minor amounts of one or more inorganic or organic salts, gums or other constituents.

A preferred carrageenan constituent for use in the invention is presently commercially available as "DANAGEL DKL" (from FMC Corp.), which is recited as being at least about 50% by weight and generally at least about 70% by weight of one or more purified carrageenan compounds mixed with lesser amounts of locust bean gum and calcium acetate.

Other carrageenan constituents which may be used in the gel compositions are those products commercially available as "Satiagel VG11S" (from Sanofi) and "Gelling Agent AF7" (from Cemcolloids).

In contrast to previously used carrageenan gel compositions, the gel composition of the present invention does not contain any added solvents, and in addition, does not contain an emulsifier in an amount conventionally used for solubilisation, as was previously thought to be necessary in carrageenan gel compositions. Furthermore, the gel composition of the invention desirably contains no, or substantially no, surfactant.

In addition, we have found that the carrageenan constituent per se can act as the gelling agent. Thus, in accordance with the present invention, it is not necessary to add additional gelling agents to commercially available carrageenan blends such as Danagel DKL during the manufacture of the gel composition.

Preferred preservatives are commercially available preservatives such as Parmetol DF 35 (from Schulke & Mayr) and Glycosyl L (from Lonza (UK) Ltd).

Preferred colorants are aqueous or, more preferably, oil-soluble dyes.

The invention allows increased levels of neat fragrance to be incorporated into the composition than is usual for a carrageenan gel, without the need to add additional ingredients to effect this.

Thus, in a preferred embodiment of the invention, the fragrance is present in an amount of 4 to 20% by weight. Preferably, the amount of fragrance is from 4 to 12% by weight, more preferably from 4 to 10% by weight.

There is no advantage to be gained from using more of the carrageenan constituent than is necessary to give an effective gel. On the other hand, there should be enough carrageenan constituent present to form a stable gel. Thus, preferably the carrageenan constituent is present in an amount of 2 to 5% by weight. Ideally, the carrageenan constituent is present in an amount between 2 and 3% by weight, and particularly at 2.3 to 2.5% by weight.

In a preferred embodiment of the invention, the gel composition consists essentially of:

a) 1 to 20% of a fragrance material,
b) 2 to 10% of a carrageenan constituent,
c) 0 to 2% of a preservative,
d) 0 to 2% of a coloring agent,
e) 0 to 0.5% surfactant, and
f) 65.5 to 97% water, all percentages being by weight of the composition, in the absence of any additional constituents, such as inorganic or organic acids or salts (other than those present in any commercially available carrageenan blend, where such a blend is used).

In some cases it may be desirable to add a small amount of surfactant as a wetting agent, although it is not necessary to add surfactant in amounts conventionally used for solubilisation. Where present, the wetting agent will comprise less than 0.5%, most preferably 0.2% or less of the composition. For example, a suitable wetting agent which may be used in the gel composition of the invention is commercially available as Crillet 4 Super from Croda Chemicals.

Further, the invention provides a method for preparing a self-supporting gel composition comprising heating water and the carrageenan constituent to a predetermined temperature, such as to 90° C., cooling to 60°–70° C. and adding the fragrance material. Optionally, one or more of a preservative, coloring agent and surfactant are also added to the composition. The composition may be moulded into an attractive shape. Thus, a preferred method includes the further step of pouring the composition into a mould before cooling.

The invention further provides a method for fragrancing rooms, cars etc. using the gel-type fragrance composition. The compositions according to the invention may comprise moulded air freshener gels which are sold packaged in a suitable wrapper that is impermeable to fragrance. The wrapper is removed before the gel is used for fragrancing the room or car, for example. The gels are physically attractive and may be displayed or placed in a suitable container. When emanation of fragrance is slow at room temperature, this can be alleviated by increasing the airflow over the gel. For example, the gel may be packaged in a moulded pack including ventilation means, which ventilation means may be opened to increase air flow over the gel.

The following examples illustrate compositions according to the present invention, methods of making them, and their use.

EXAMPLE 1

The composition (detailed in the table below) was made up by heating the carrageenan gelling agent and water to a temperature of 90° C. while stirring for 30 minutes.

This composition was then cooled to 70° C. and then the fragrance and preservation and color were added and stirred well for a further 15 minutes.

This composition was then poured into a mould and allowed to cool to room temperature over 20 minutes.

The composition formed was as follows.

TABLE

| | |
|---|---|
| 2.5% | of the carrageenan constituent, Danagel DKL (from FMC) |
| 10.0% | of the fragrance, Pavlova K28552 (from Robertet) |
| 0.1% | of the preservative, Parmetol DF35 (from Schulke & Mayr) |
| 0.001% | of a colourant such as Dragoco (from Sandoz), the balance being water |

EXAMPLE 2

Example 1 is repeated using a 2.5% Satiagel VG11S as the carrageenan gelling agent in place of 2.5% Danagel DKL.

EXAMPLE 3

Example 1 is repeated using a 2.3% gelling agent AF7 as the carrageenan gelling agent in place of Danagel DKL.

EXAMPLE 4

Example 1 is repeated using a 5% DKL as the carrageenan gelling agent instead of 2.5% Danagel DKL.

Examples 1 to 4 are repeated using 1.5%, 3.0%, 6.0%, 12.0% and 20.0% of the fragrance material instead of 10% of the said fragrance material.

EXAMPLES 5–13

Example 1 is repeated using the fragrances given below instead of 10% of Pavlova.

Example 5: 10% of Charlotte 56 from Givaudan

Example 6: 10% of Frangipan 36 from Givaudan

Example 7: 10% of Summer Pudding K/28552 from Robertet

Example 8: 10% of Pineapple Parfait K/28555 from Robertet

Example 9: 10% of Lemon Soufflé K/28554 from Robertet

Example 10: 10% of Tartufi K/28594 from Robertet

Example 11: 10% of LQ 51898 Pot Pourri from Bush Boake Allen (BBA)

Example 12: 10% of LQ 51899 Lavender from BBA

Example 13: 10% of Neutrair LQ 51759 from BBA

Examples 5–13 are repeated using 1.5%, 3.0%, 6.0%, 12.0% and 20.0% of the fragrance material instead of 10% of the said fragrance material.

EXAMPLES 14–22

Examples 5–13 are repeated using 2.3% of Satiagel VG11S from Sanofi in place of 2.5% of Danagel DKL.

EXAMPLES 23–31

Examples 5–13 are repeated using 2.3% of gelling agent AF7 in place of 2.5% of Danagel DKL.

EXAMPLES 32–40

Examples 5–13 are repeated using 5% of Danagel DKL as the carrageenan gelling agent instead of 2.5% Danagel DKL.

I claim:

1. An aqueous self-supporting gel composition consisting essentially of:

a) 1 to 20% of a fragrance material, b) 2 to 10% of a carrageenan constituent, c) 0 to 2% of a preservative, d) 0 to 2% of a coloring agent, and the balance being water and all percentages being by weight of the composition.

2. A composition according to claim 1, in which the carrageenan constituent is present in an amount of from 2 to 5% by weight.

3. A composition according to claim 1, in which the fragrance material is present in an amount of from 4 to 20% by weight.

4. A composition according to claim 3 in which the fragrance material is present in an amount of from 4 to 10% by weight.

5. An airfreshener composition according to claim 1.

6. The aqueous self-supporting gel composition according to claim 1 wherein the carrageenan constituent comprises at least about 50% by weight of one or more carrageenan compounds.

7. The aqueous self-supporting gel composition according to claim 1 wherein the carrageenan constituent comprises at least about 70% by weight of one or more carrageenan compounds.

8. An aqueous self-supporting gel composition according to claim 1 consisting essentially of:

a) 1.5–20% of a fragrance material;

b) 2.3–5% of a carrageenan constituent;

c) 0–2% of a preservative;

d) 0–2% of a coloring agent;

the balance to 100% by weight water.

9. The aqueous self-supporting gel composition according to claim 8 wherein the carrageenan constituent comprises at least about 50% by weight of one or more carrageenan compounds.

10. An aqueous self-supporting gel composition consisting essentially of:

a) 2.5% of a carrageenan constituent, b) 10% of a fragrant material, c) 0.1% of a preservative, and d) 0.001% of a coloring agent, the balance to 100% being water and all percentages being by weight of the composition.

* * * * *